United States Patent [19]

Hathaway

[11] Patent Number: 5,295,949
[45] Date of Patent: Mar. 22, 1994

[54] MODULAR NECK APPARATUS

[76] Inventor: Charles Hathaway, 11905 NE. Glisan St., Portland, Oreg. 97220

[21] Appl. No.: 946,567

[22] Filed: Sep. 18, 1992

[51] Int. Cl.⁵ .................................. A61F 5/02
[52] U.S. Cl. ........................ 602/18; 482/10; 482/140; 602/14; 607/109
[58] Field of Search .............. 602/2, 14, 17, 18, 74; 128/DIG. 23, 402, 403, 118.1; 2/44, 45; 482/10, 11, 74

[56] References Cited

U.S. PATENT DOCUMENTS

| | | | |
|---|---|---|---|
| 450,188 | 4/1891 | Peterson | 482/10 |
| 554,636 | 2/1896 | Hulsmann | |
| 1,012,802 | 12/1911 | Brogan | |
| 1,343,357 | 6/1920 | Eggers | 128/118.1 X |
| 1,964,655 | 6/1934 | Williamson | |
| 3,374,785 | 3/1968 | Gaylord, Jr. | 602/18 |
| 3,819,177 | 6/1974 | Spiro | |
| 3,964,474 | 6/1976 | Fox | 128/DIG. 23 X |
| 4,204,674 | 5/1980 | Ogland | |
| 4,335,875 | 6/1982 | Elkin | 482/74 |
| 4,337,938 | 7/1982 | Rodriguez | 482/74 |
| 4,576,169 | 3/1986 | Williams | 128/402 |
| 4,691,917 | 9/1987 | Battista | 482/74 X |
| 4,742,827 | 5/1988 | Lipton | |
| 4,756,306 | 7/1988 | Curlee | |
| 4,756,525 | 7/1988 | Whitshitt | |
| 4,762,318 | 8/1988 | Phillips | |
| 4,865,012 | 9/1989 | Kelley | 128/403 X |
| 4,966,136 | 10/1990 | Bates | 602/18 |
| 5,005,374 | 4/1991 | Spitler | 128/402 X |
| 5,029,577 | 7/1991 | Sarkozi | 602/18 |
| 5,088,487 | 2/1992 | Turner | 128/402 |
| 5,211,623 | 5/1993 | Sarkozi | 602/18 |

FOREIGN PATENT DOCUMENTS 559138  2/1923  France .

Primary Examiner—Richard J. Apley
Assistant Examiner—Beverly A. Meindl
Attorney, Agent, or Firm—Robert L. Harrington

[57] ABSTRACT

A modular apparatus comprising a neck band and a variety of inserts to provide different functional capabilities useful and beneficial for the treatment of an injury to the neck and the rehabilitation associated therewith. The neck band is provided with a pocket for receiving the interchangeable insertion of the various inserts. One of the inserts in conjunction with the neck bank provides an apparatus for immobilizing or limiting movement of the neck. A cylindrical insert in conjunction with the neck band provides an apparatus beneficial for improving articular motion of the joints of the neck. An insert filled with a medium that may be either heated or cooled in conjunction with the neck band provides either a hot pack or a cold pack. The neck band is of an elastic material and has formed loops on each of its ends to facilitate utilization of the neck band for exercise routines, either by using the band by itself or using the band with one of the inserts inserted in the pocket. The neck band has self adhering fasteners affixed at each of its looped ends for ease of fitting the band to the neck of an individual.

2 Claims, 3 Drawing Sheets

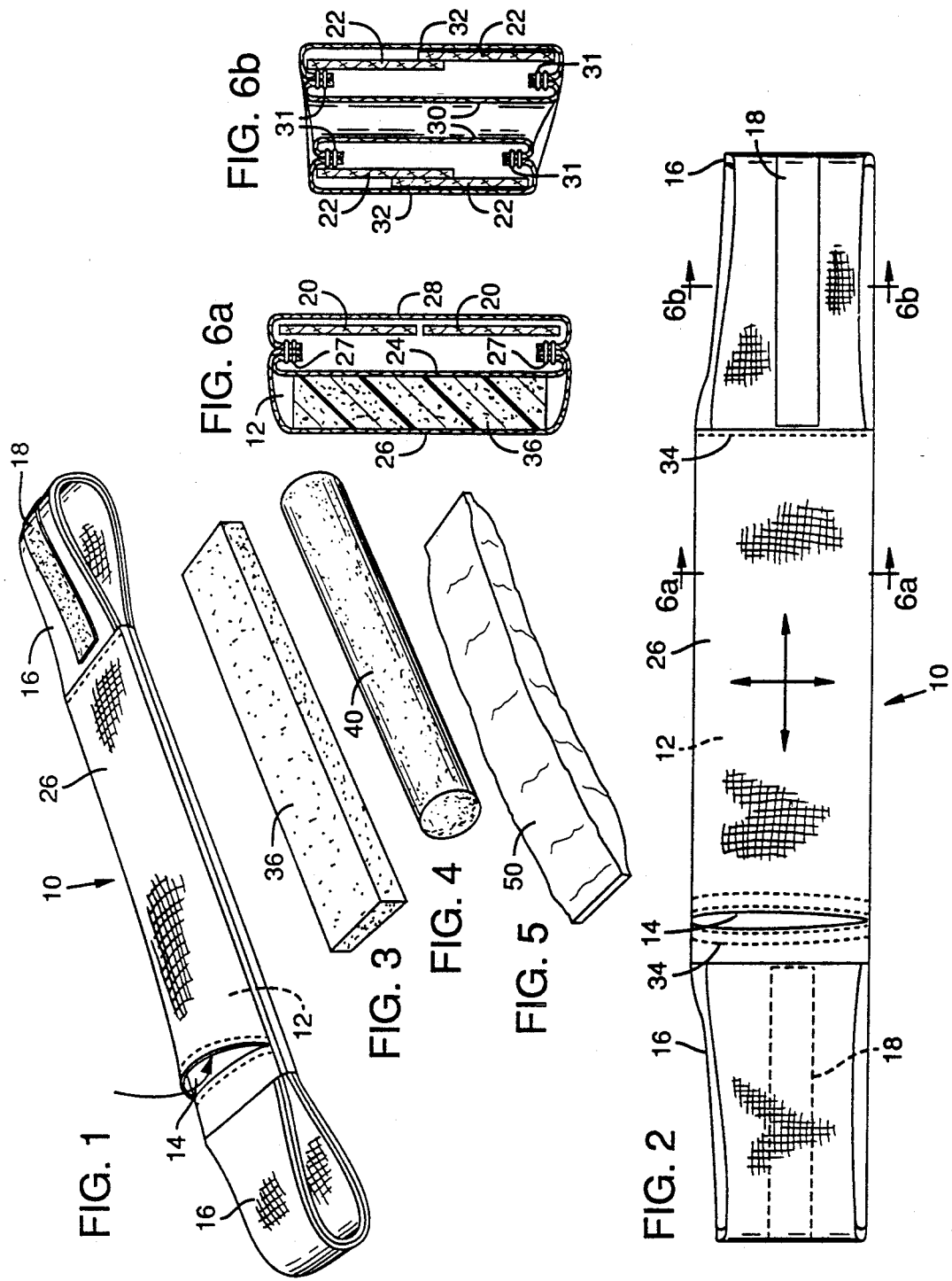

MODULAR NECK APPARATUS

BACKGROUND OF THE INVENTION

Field of the Invention

This invention relates to devices used in the treatment of neck injuries and particularly it relates to modular apparatus that is convertible to provide a variety of functions for the treatment of neck injuries and rehabilitation associated with the treatment.

Neck injuries, whether they be severe or mild, are a discomfort to one who suffers such a malady. An individual suffering a neck injury will, for a rapid and most complete recovery, progress through a series of different treatments during recovery and rehabilitation. The treatment of neck injuries including rehabilitation generally is accomplished by use of many different devices to aid in the recovery process, provide comfort to the individual and as aids in exercising.

The treatment of the injury and the rehabilitation required may include, for example, the application of cold packs, immobilization of the neck, the application of hot packs, and various forms of exercises. Each of the treatment routines is accomplished or at least assisted by the use of separate devices or implements. The application of cold packs is accomplished by placing ice or a chilled liquid in an ice bag or similar device and applying the bag to the area of the injury. Hot packs are similarly applied to an area of the injury by using a device such as a hot water bottle or the like which is most often filled with heated water. The neck is most often immobilized by the use of a collar fitted around the neck. The collar is usually a semi-rigid elongate member covered with a cloth material which is configured to have a height to fit under the chin and the rear of the head with the bottom of the collar resting generally on the shoulder area of the individual. Fasteners are provided at each of its ends for fastening the collar in position once it is wrapped around the neck. There are numerous exercising devices utilized to provide exercise routines for increasing the strength of the muscles and mobility of the joints associated with neck movement.

Each phase or routine in the treatment and rehabilitation of the neck is thus enhanced or aided by the employment of a variety of different devices or implements. An individual, in order to fully benefit from each phase of the treatment, must then have at his/her disposal all of the different implements or devices to affect the best results of each phase or routine utilized in the treatment and/or rehabilitation.

It is an object of the present invention to provide a modular apparatus that is convertible to provide an apparatus arranged for each phase or routine.

BRIEF SUMMARY OF THE INVENTION

The present invention is a modular apparatus that may be arranged by the interchange of modules to provide different functional capabilities desired in treating an injury to an area of the neck and the rehabilitation associated with the treatment. The modular apparatus by the appropriate interchange of modules provides the capability of applying hot or cold packs to an injured area, provides the capability of immobilizing or limiting the movement of the neck, provides the capability of aiding the articular motion of the neck joints and provides the capability of aiding in exercise routines including isotonic and isometric.

A preferred embodiment of the invention is a pocketed neck band and a number of modular interchangeable pocket inserts. The neck band is an elongate elastic member being of a suitable length and configuration to fit around the neck of an individual. Loops are provided on each end of the band sufficiently large to permit insertion of an individual's hands. Fasteners ar provided on the looped ends of the band to facilitate fitting and securing the band in position around the neck. A pocket is provided in the band and the pocket has an opening for ease of insertion and removal of interchangeable inserts. The band in conjunction with an insert provides a functional capability desired in the treatment of an injury or the rehabilitation associated with the treatment. A rectangular insert is provided that is insertable in the pocket of the band which provides an apparatus that when fitted to the neck will immobilize or limit movement of the neck. A cylindrical insert is provided that is insertable in the pocket of the band which provides an exercising apparatus for improving the articulation of the joints of the neck. An insert in the form a rectangular container which is filled with a material that may be heated or cooled is insertable in the pocket of the band to provide either a hot pack or a cold pack depending on whether the filled container is heated or chilled. In addition to the band being utilized in conjunction with the interchangeable inserts to provide individual functional capabilities, the band may be utilized without any inserts. The band, used by itself, is an excellent exercise device for both isotonic and isometric exercise routines. The band being elastic enables a user to apply a force which is to be resisted in an isometric manner by the muscles of the neck or in the alternative the neck may be moved against (or with) the applied force for an isotonic exercise routine. The formed loops on the ends of the band enable a user to place the band around the rear of the head or neck, around the forehead or to either side of the head and apply a force by stretching the band. The loops allow placement of the band. The force applied for either isotonic or isometric exercising is dependent on the degree the band is stretched. Additionally the band is an excellent device for stretching and warm up exercises preparatory to the user engaging in physical activities.

Refer now to the drawings and the detailed description for a complete understanding of the invention.

BRIEF DESCRIPTION OF THE DRAWINGS

FIG. 1 is a view of the neck band of the present invention;

FIG. 2 is another view of the neck band of the present invention;

FIG. 3 is a view of a semi-rigid insert installable in the neck band of FIG. 1;

FIG. 4 is a view of a cylindrical insert installable in the neck band of FIG. 1;

FIG. 5 is a view of packet insert installable in the neck band of FIG. 1;

FIGS. 6a and 6b are views as viewed on view lines of 6a—6a and 6b—6b of FIG. 2 showing the inner structure detail and the insert of FIG. 3 installed in the pocket of the neck band;

DESCRIPTION OF THE PREFERRED EMBODIMENT

Figure 7:
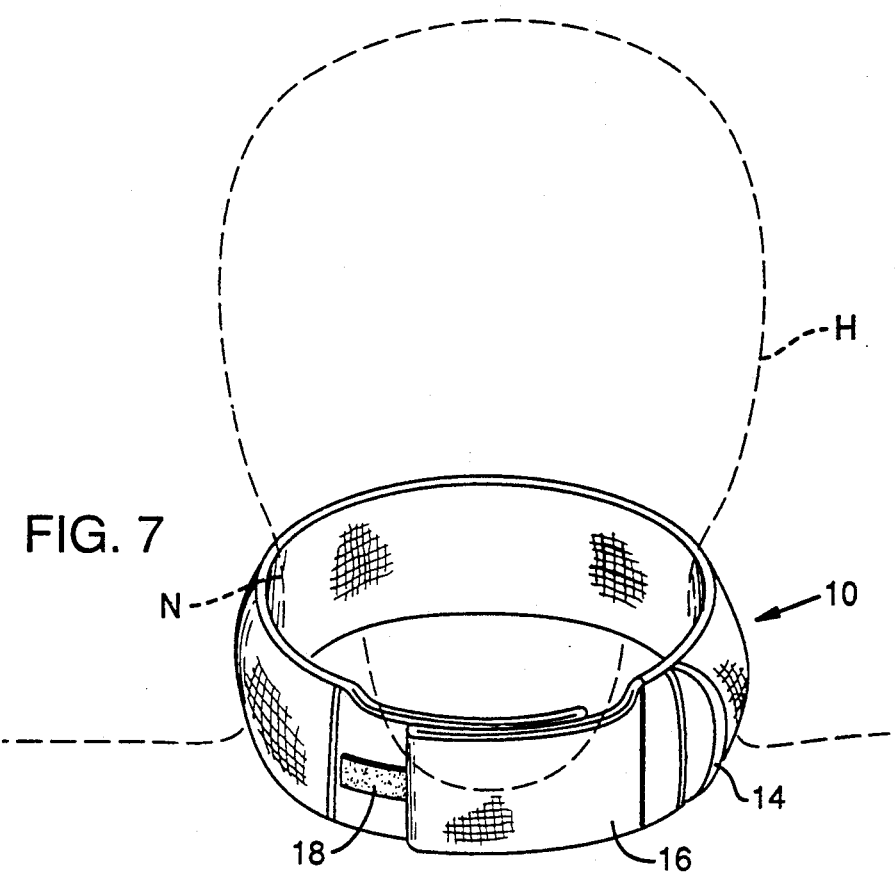
FIG. 7 is a view of the neck band of FIG. 1 fitted to the neck of an individual.

The present invention is a modular apparatus that is convertible by the interchange of inserts to provide a variety of implementations that are beneficial in the treatment of an injured area of the neck and rehabilitation associated with the treatment. The foundation of the modular apparatus is an elongate band of elastic material that has a formed pocket for receiving the interchange of modular inserts. The inserts installed in the band provide a specific implement to be used in the treatment and rehabilitation of an injured area of the neck.

Refer now to FIGS. 1 and 2 of the drawings. These drawings illustrate an elongate elastic neck band 10, preferably of an elastic material that is soft and comfortable to the touch and is resiliently stretchable. The band 10 is constructed as by sewing using well known techniques of the trade. A formed pocket 12 is provided in the band 10 as illustrated for receiving inserts as will later be described. The pocket 12 has an opening 14 at one end to facilitate the insertion and removal of the inserts. Loops 16 are provided at each end of the band 10 which are basically the same width as the band 10 and are sufficiently large to permit the insertion of an individuals hand. Self adhering fasteners 18, such as VELCRO, are attached to each of the loops 16. The band 10 is preferably of layered construction as illustrated and best seen in FIGS. 6a and 6b. A stiffener 20 is provided within the band 10 adjacent to and along the length of the pocket 12 as illustrated in FIG. 6a and similarly a stiffener 22 is provided within the loops 16 as illustrated in FIG. 6b. The stiffeners 20, 22 are preferably of a web like material that aid in maintaining the band 10 in a flat configuration. The stiffeners 20, 22 are however highly flexible and will conform to the bend of the band 10. The stiffeners 20, 22 are fitted within the band 10 so as not to interfere with the stretching capability of the band 10 in either of the axial directions. Typically the stiffeners are merely basted at one edge or are simply fit within the cavities of the band 10 as illustrated in FIGS. 6a and 6b.

Refer to FIGS. 6a and 6b which show the layered construction of the band 10. The insert 36 is shown received in the pocket 12 in FIG. 6a. The band 10 is fabricated from layered material having an inner wall 24 and outer walls 26 and 28. The walls 24, 26, and 28 are joined together at their edges by stitching 27. The inner wall 24 and the outer wall 26 cooperatively form the insert receiving cavity referred to as the pocket 12. As previously mentioned, the pocket 12 has an opening 14 which is provided in the wall 26 as shown in FIGS. 1 and 2. The inner wall 24 and the outer wall 28 form another cavity for receiving the stiffeners 20. The loops 16 are similarly constructed having in inner wall 30 and an outer wall 32 joined at their edges by stitching 31. The inner wall 30 and outer wall 32 cooperatively form a cavity to receive the stiffeners 24. The walls 30, 32 of the loops 16 are joined by stitching 34 to the walls 24, 26, and 28 to complete the band 10.

The band 10 is of sufficient length so that it may be wrapped and fitted around the neck of an individual and secured in position by the mating engagement of the self adhering fasteners 18. The band 10 with an insert installed in the pocket 12 provides an apparatus or implement that is an aid in treating and rehabilitating an injury to the neck. The type of insert installed in the pocket 12 determines the function of the apparatus. The different types of inserts useable with the band 10 will now be described. The band 10 is shown fitted around the neck of an individual in FIG. 7 and is shown partially wrapped around the neck in FIG. 8. The neck is generally indicated by the letter N in the figures, the head of the individual generally indicated by the letter H and the hands generally indicated by the letter L. It will be appreciated that the individual is merely shown in a dashed silhouette so as not to detract from the drawing of the band 10.

Refer now to FIG. 3 of the drawings. An immobilizing insert 36 is illustrated that is installable in the pocket 12 of the band 10. The insert 36 is basically rectangular in shape and is preferably of a semi-rigid material such as foam. The insert 36 is pliable permitting it to conform to a curvature such as the neck of an individual. The insert 36 is yieldably compressible yet is of sufficient rigidity to act as a supporting member, particularly when it is installed in the pocket 12. The band 10 with the insert 36 installed in the pocket 12 will when fitted around the neck of an individual provide a neck band utilized to immobilize or limit the movement of the neck.

Figure 8:
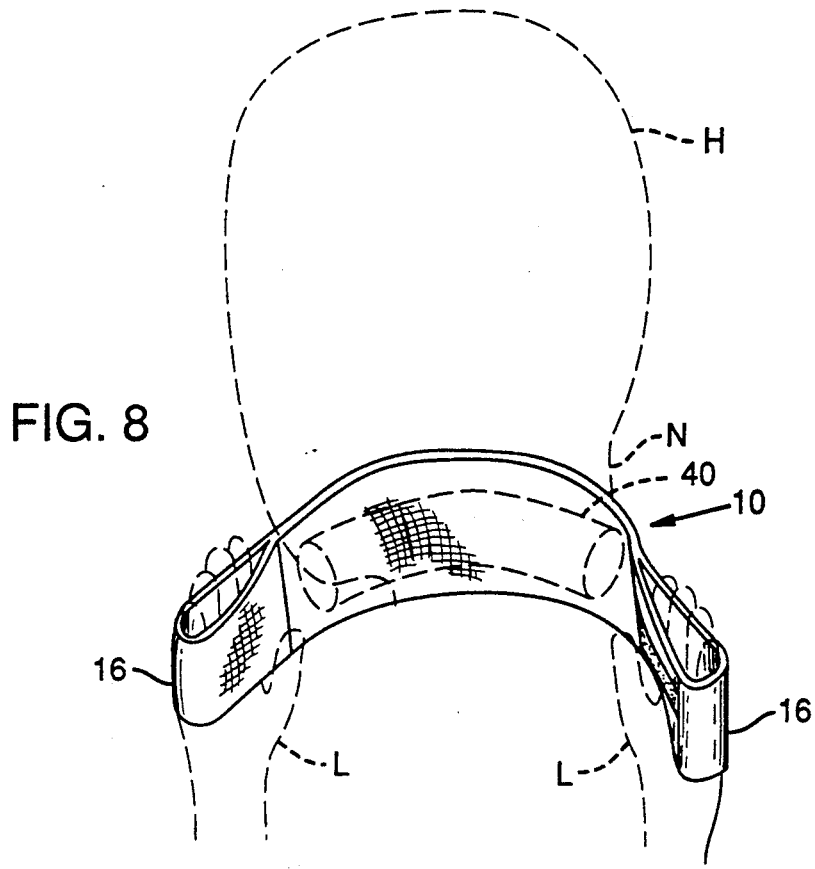
FIG. 8 is a view of the neck band of FIG. 1 with the insert of FIG. 4 installed in the neck band.

FIG. 4 illustrates a cylindrical insert 40 installable in the pocket 12 of the band 10. The insert 40 is preferably of a pliant resilient material such as foam. The insert 40 installed in the band 10 provides a device that is an aid in articular exercising. One method of use is shown in FIG. 8 where a user will hold the pocket area of the band in position against an area of the neck. The hands of a user fitting in the loops 16 are a benefit for placing the band 10 in the desired position. While only one position is shown in FIG. 8, it is apparent that the band may be positioned against other areas of the neck by altering the position of the hands. Movement of the neck against the insert 40 installed in the band 10 will thus urge articulation of more than one joint of the neck. The band 10 with the insert 40 may also be utilized with the band secured around the neck as illustrated in FIG. 7.

FIG. 5 illustrates an insert 50 installable in the pocket 12 of the band 10 and is preferably a self contained container filled with a material, such as a gel, that is suited to be either cooled or heated. The insert 50 is utilized to either transfer heat to and transfer heat from the neck area. The insert 50 is chilled as by placing in a freezer and then is installed in the pocket 12 of the band 10 to serve as a cold pack. The band 10 with the chilled insert 50 may be fitted to the neck of the individual as illustrated in FIG. 7 to cool the injured area or it may be merely topically placed against an area of the neck in a conventional manner. The insert 50 may be heated as by immersing in hot water or by a microwave oven. The heated insert installed in the band 10 thus may be fitted to the neck of an individual as shown in FIG. 7 or it may be selectively placed against a specific area of the neck to provide a hot pack.

The band 10 fitted with one of the inserts described and illustrated provides a variety of functions suited for aiding the treatment of an injury to the neck and the rehabilitation associated with the treatment. The band 10 with the insert 36 fitting in the pocket 12 will provide an immobilizing collar to limit the motion of the neck of an individual. The band 10 with the insert 40 fitting in the pocket 12 provides an articular exercising device.

The band 10 with the insert 50 fitting in the pocket 12 provides a device for either applying hot or cold packs depending on whether the insert 50 is heated or cooled.

Figure 9:
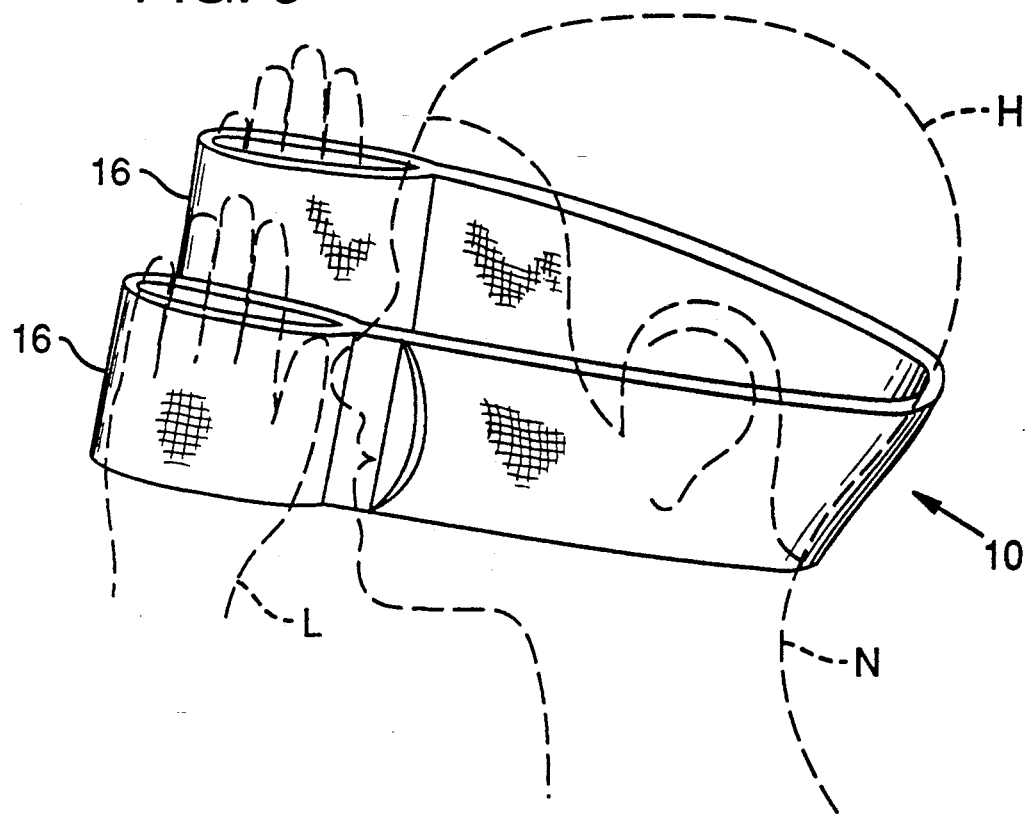
FIG. 9 is view showing an individual using the neck band of FIG. 1 as an exercise device.

Additionally the band 10 may be utilized separately without an insert as an aid in performing other exercises. FIG. 9 illustrates one method of using the band as an exercising device. As shown, the band 10 is positioned around the back of the head with the individuals hands in the loops 16 of the band. The user may apply a force to the head and thus to the neck by stretching the band by extending the hands forwardly. The user may, at his/her option perform either isometric type exercising or isotonic type exercising. By maintaining the head in a fixed position (neck muscles isometric), the user may alter the force by movement of the hands. The neck muscles will thus be simply resisting the force applied. In the alternative the hands may be extended to apply a force and the head may be moved forward and rearward with and against the force to perform an isotonic exercise of the neck muscles, since the forward and rearward movement of the head employs the muscles of the neck. While only one arrangement has been shown utilizing the band as an exercising device, a user may position the band in alternative positions to apply a force in other directions. The band may for example be placed against the forehead of the individual and the hands moved rearward to apply a force to the front of the head. Similarly the band may be positioned on either side of the head to apply a lateral force to the head. The band 10 also provides a useful device for stretching and warm up exercises for an individual that will be engaging in a physical activity.

Those skilled in the art will recognize that variations and modifications may be made without departing from the true spirit and scope of the invention. The invention is therefore not to be limited to the embodiments described and illustrated but is to be determined from the appended claims.

What is claimed is:

1. A device for rehabilitation of a neck injury to a patient comprising:

an elongate neck band having a flexible elongate center portion and end portions, said elongate center portion comprised of a soft elastic material and configured to fit flat against a patient's neck with a width and length that substantially covers the neck area of a patient, said end portions configured to form handles that can be gripped by the patient's hands and with the soft elastic center portion wrapped around the back of the patient's neck the patient can pull on the handles to stretch the band against the resistance of the neck muscles for isometric and isotonic exercising of the neck muscles;

said center portion of the neck band having a pocket that substantially extends the length and width of the center portion and an opening to the pocket, and a rectangular immobilizing insert that fits the pocket length and width, said insert of a semi-rigid material that yieldingly resists deformation and is substantially more rigid than the center portion of said neck band, said insert inserted into said pocket to convert the center portion into a neck support when wrapped around a patient's neck, and mated fasteners on the end portions for securing the end portions together and thereby securing the center portion of the band in place around a patient's neck for support of the patient's neck; and a flexible container containing a fluid material having the property of being selectively cooled and heated, said flexible container sized to fit the pocket of the flexible center portion of the band and when inserted into the pocket with the band attached to the patient's neck, providing therapeutic cooling or heating of the patient's neck.

2. A device as defined in claim 1 including a cylindrical insert of pliant resilient material, said cylindrical insert sized to fit the pocket of the flexible center portion of the band and converting the flexible band into a substantially cylindrical configuration, and with the cylindrical insert inserted into the pocket and the band placed around the back of the patient's neck and with the patient's hands gripping the end portions, providing an aid for articular exercising.

* * * * *